United States Patent [19]
Hoffman et al.

[11] Patent Number: 4,931,547
[45] Date of Patent: Jun. 5, 1990

[54] MONOCLONAL ANTIBODIES TO LEGIONELLA

[75] Inventors: Paul S. Hoffman, Memphis, Tenn.; Leta O. Helsel, Atlanta, Ga.; William F. Bibb, Decatur, Ga.; Roger M. McKinney, Dunwoody, Ga.

[73] Assignee: The University of Tennesse Research Corporation, Knoxville, Tenn.

[21] Appl. No.: 205,625

[22] Filed: May 31, 1988

Related U.S. Application Data

[63] Continuation of Ser. No. 838,685, Mar. 12, 1986.

[51] Int. Cl.$^5$ .................... C07K 15/28; C12N 5/20
[52] U.S. Cl. ..................... 530/387; 530/806; 530/809; 435/240.27; 435/70.21; 435/948; 435/7; 436/548; 935/104; 935/108; 935/110
[58] Field of Search ............. 530/387, 388, 806, 809; 435/240, 27, 7, 68, 70.21, 948; 436/548; 424/85.8; 935/100, 104, 108, 110

[56] References Cited

U.S. PATENT DOCUMENTS 4,514,509  4/1985  Kohler et al. ................. 436/518

OTHER PUBLICATIONS

Bulter, C. A. et al., Infect. Immun., 48(1):14–18 (1985).
Larry H. Gostling et al, Identification of a Species-Specific Antigen in *Legionella pneumophila* by a Monoclonal Antibody, Dec. 1984, Journal of Clinical Microbiology, pp. 1031–1035, vol. 20, No. 6.
FDA ok's Test For Legionnair's Disease—Published in Biotechnology News, p. 8, Aug. 15, 1984.
Scots Monitor for Legionnaire Bugs—Published in Chem. Ind., 11:348 (1985).

*Primary Examiner*—Garnette Draper
*Assistant Examiner*—Kay E. Cheney
*Attorney, Agent, or Firm*—Luedeka, Hodges & Neely

[57] ABSTRACT

Monoclonal antibodies demonstrating reactivity to genus-specific epitopes present on outer membrane proteins of bacteria of the genus Legionella and hybridomas for secreting the antibodies are disclosed.

7 Claims, No Drawings

MONOCLONAL ANTIBODIES TO LEGIONELLA

The U. S. government has rights in this invention pursuant to National Institute of Health grant No. AI 20867-02.

This application is a continuation of application Ser. No. 838,685, filed Mar. 12, 1986.

The present invention relates to monoclonal antibodies and hybridomas and more particularly relates to monoclonal antibodies reactive to genus-specific epitopes present on outer membrane proteins of the bacterial genus Legionella and hybridomas for producing the antibodies.

Since the report of 34 fatal cases of Legionnaire's Disease following the American Legion Convention in Philadelphia in 1976 and subsequent identification of the bacteria *Legionella pneumophila* as the cause, bacteria of the genus Legionella have been recognized as significant pathogens. Currently, at least 25,000 new cases of Legionnaire's disease are reported each year. In addition, Legionella are believed to be responsible for at least 10% of atypical pneumonias of unknown cause. Legionellae are also known to cause milder ailments such as the nonpneumonic respiratory disease referred to as Pontiac fever. Because Legionella can live in air conditioning cooling water systems and in the water supply systems of buildings, epidemics of Legionnaire's disease are a threat in hospitals and other buildings.

Legionellae are gram-negative bacteria and thus have an outer membrane forming part of the cell wall. Twenty-two species of Legionella have been identified which are classified into numerous serogroups depending upon the immunological response of a host to the bacteria. While the species *Legionella pneumophila* is the primary etiological agent of Legionnaire's disease, some of the other species are now also recognized as causing Legionnaire's disease and other ailments.

Various tests are available for diagnosing Legionnaire's disease and for identifying the bacteria in clinical specimens and in environmental samples. Many, however, are time consuming such as testing for the presence of antibodies in serum of the patient or isolation and culture of the bacteria from clinical specimens. Often, a patient must be treated for Legionnaire's disease before it is confirmed that a patient has the disease. Other tests such as direct fluorescent antibody tests with polyclonal antibodies are rapid but mixed antibody reagents are necessary to indentify the multiple serogroups. In fact, several antibody reagents are necessary to identify all of the eight serogroups of just the species *Legionella pneumophila*. In addition, there are problems with cross-reactions with strains of other bacteria since the lipopolysaccharides of the outer membrane are similar to other bacteria, e.g., Pseudomonas.

Monoclonal antibodies have been developed recently which are specific to the species *Legionella pneumophila* as reported by L. Gosting et al in "Identification of a Species-Specific Antigen in *Legionella pneumophila* by a Monoclonal Antibody", J. Clin., Microbiol 20:1031–1035 (1984). While these monoclonals are useful in immunofluorescence and other assays for *L. pneumophila*, they cannot be used to detect the other species of Legionella. A monoclonal specific to *L. pneumophila* has also been reported in Chem. Ind. 85:348 which is stated to be most useful for for monitoring the presence of the organism in cooling towers, condensors, and other water systems.

It is therefore an object of the present invention to provide monoclonal antibodies which are specific to the genus Legionella.

In accordance with the invention, there are provided monoclonal antibodies which are genus-specific for Legionella and hybridomas for producing them. The invention is based on the discovery that genus-specific epitopes are present in outer membrane proteins of Legionella. The term "genus-specific epitope" is intended to refer to antigenic sites on outer membrane proteins which are essentially unique to the genus Legionella whether or not the epitope is available in intact Legionella cells to illicit an immunological response in a host. The epitope may vary slightly in amino acid composition from species to species.

Hybridomas for secreting the antibodies of the invention are produced from the outer membrane proteins which have been isolated with sufficient purity to elicit an immunological response to the genus-specific epitope in an animal which has been vaccinated with the purified outer membrane protein. Lymphocytes from the animal are fused with myeloma, plasmacytoma or hybridoma cells to form cell hybrids which are selected for secreting antibodies reactive to the genus-specific epitopes.

The preparation of the outer membrane proteins first involves the separation of outer membrane materials from Legionella cells. This is suitably accomplished by mechanical lysing of the cells and separating of outer membrane fractions by sucrose gradient. Alternately, separation of outer membranes can be done by extraction of whole cells with sodium N-lauroyl sarcosinate followed by pelletizing outer membranes by ultracentrifugation.

Outer membrane proteins having genus specific epitopes are then isolated from the outer membrane materials. In order to separate the desired proteins from lipopolysaccharides which elicit a strong immunological response and would thus interfere with antibody production to the desired proteins, it has been found that it is necessary to reduce the outer membrane protein oligomers to soluble monomers. For *L. pneumophila*, this is preferably carried out by extraction of the proteins from membrane material with 2-mercaptoethanol and boiling in 2% SDS for 10 minutes. The solubilized material is subjected to gel filtration to separate extracted proteins from the outer membrane LPS material. The method also separates proteins which contain genus-specific epitopes. The molecular weights of proteins in the fractions are suitably monitored by SDS-polyacrylamide gel electrophoresis. For *L. pneumophila*, outer membrane proteins with genus-specific epitopes have been identified as proteins having an apparent molecular weight of 28 kDa and 60 kDa against Pharmecia molecular weight standards. It is believed that the 60 kDa protein may be a dimer of the 28 kDa protein which forms during isolation of the proteins as described in this patent application and also in the biological degradation of the bacteria so as to be present in blood and in urine. Other outer membrane proteins of other species of Legionella can be isolated similarly to *L. pneumophila*, e.g., *L. oakridgensis* (26 kDa protein) and *L. micdadei* (35 kDa protein).

The purified proteins are then used to stimulate animals for in vivo antibody production. After immunization, immune lymphocytes from the immunized animal are fused to myeloma cells, plasmacytoma cells or hybridoma cells which secrete no immunoglobulin, to generate hybridoma cell lines which can be cultured indefinitely to produce monoclonal antibodies. The lymphocytes are taken either from lymph node tissue or spleen tissue with immune spleen cells being preferably employed. Generally, fusion techniques are employed as are known in the art such as the procedures set forth in Kohler et al Eur. J. Immunol. 6:11–19 (1976) and Kennett et al, Lymphocyte Hybridomas-Current Topics in Microbiology and Immunology 81:77–91 (1978) Springer-Verlag, New York. Fusion is suitably accomplished by addition of a suspension of antibody producing cells to the myeloma cells in growth medium and centrifuging to form a pellet.

The hybridomas are screened for antibody production specific for outer membrane proteins by, for example, an enzyme-linked immunoabsorbent assay using outer membrane materials from the species used in producing the hybrids. The selected hybrids are further screened for being specific to the genus by running an assay with outer membrane materials from several species of Legionella. These selected hybrids are cultured to establish a continuous cell line with stable genetic coding.

The monoclonal antibodies of the present invention can be employed in a variety of techniques for the diagnosis of Legionnaire's disease and for the detection of the bacteria in environmental samples. Samples are treated mechanically, for example, to disrupt the cells and expose the antigen for reaction with the antibody which has been labelled. In some instances, the free antigen is present in the sample, e.g., blood or urine, and treatment to disrupt the cells is not necessary. The monoclonal antibodies are particularly well-suited for antigen capture assays with colorimetric reagents such as enzyme-linked immunoabsorbent assays.

The following examples illustrate various embodiments of the invention without any intent to limit the invention to the embodiments disclosed.

Examples I and II illustrate the preparation of outer membrane materials of *L. pneumophila*. Example III illustrates large scale production of 28 kDa and 60 kDa outer membrane proteins from the outer membrane materials of *L. pneumophila*. Example IV illustrates the preparation of hybridomas secreting monoclonal antibodies to the 28 kDa outer membrane protein isolated as in Example III. Example V illustrates the preparation of a hybridoma secreting monoclonal antibodies to the 60 kDa outer membrane protein isolated as in Example III. Example VI illustrates the use of antibodies in diagnosing Legionnaire's disease. Example VII illustrates use of antibodies of the invention to detect Legionella in an air conditioning cooling water system.

EXAMPLE I

*L. pneumophila cells* are lysed in a French press and crude membrane material is obtained. The cytoplasmic and outer membrane fractions are separated by layering crude membranes onto 15% (wt/vol) sucrose-3 mM EDTA (18 ml) with a cushion of 70% (wt/vol) sucrose-3 mM EDTA (3 ml) and centrifuging in an SW28.1 rotor at 25,000 rpm for 2 h. A total membrane fraction is collected from the 15%/70% sucrose interface. The outer membrane then is separated from the inner membrane by a step gradient containing five equal-volume fractions of sucrose each containing 3 mM EDTA: 50, 55, 60, 65, and 70%. A band at the 60%/65% interface contains the outer membrane material as judged by the presence of 2-keto-3-deoxyoctonic acid and the absence of NADH dehydrogenase and succinate dehydrogenase activities.

EXAMPLE II

Outer membranes are obtained by extraction of whole *L. pneumophila* cells with sodium N-lauroyl sarcosinate (Sarkosyl: Sigma). By this method, cells from a 24- to 48-h-old BYCE agar slant are suspended in 5 ml of 50 mM Tris hydrochloride (pH 7.2) to an optical density of 0.2, pelleted by centrifugation (10,000×g for 15 min), and are disrupted with 2% Sarkosyl in 50 mM Tris hydrochloride (pH 7.2). After 1 h of incubation at 37° C., DNA is sheared by ultrasonic vibration (15 s at a setting of 6 on a model 185 Sonifier Cell Disruptor; Heat Systems-Ultrasonics, Inc. Plainview, N.Y.). Unbroken cells are removed by low-speed centrifugation, and outer membranes are pelleted by ultra centrifugation at 100,000×g for 30 minutes. Lysozyme (1 mg/ml) is added, and incubation was resumed for 1 h at 37° C. The material is pelleted by centrifugation at 100,000×g for 30 minutes to obtain outer membranes.

EXAMPLE III

For large scale production of 28 and 60 kDa proteins, 20 to 50 g wet weight of cells are grown in BYE broth, harvested by centrifugation and lysed by passage through a French pressure cell (2X). The cell free extract is obtained by low speed centrifugation and a total membrane fraction is obtained by ultracentrifugation at 100,000×g for 60 minutes. At this stage, lysozyme treatment can be used to remove contaminating peptidoglycan. The material is suspended in sarkosyl which solubilizes the cytoplasmic membrane and centrifugation at 100,000×g pellets the outer membrane fraction. The outer membrane fraction is then suspended in 2% SDS and 10% 2-mercaptoethanol and boiled for 10 minutes to solublize the 28 kDa and 60 kDa proteins. These are then chromatographically separated by gel filtration on a Sephadex G-75 column equilibrated in 0.1% SDS in Tris buffer, pH 8.0. SDS-PAGE (polyacrilamide gel electrophoresis) is employed to determine molecular weights as described below. The 28 and 60 kDa proteins are well separated by this step and are essentially pure.

The molecular weights are determined by SDS-PAGE in one dimension at a constant current of 30 mA in 11% gradient vertical slab gels containing 0.1% SDS in a Tris-glycine system. Gels are stained with Coomassie brilliant blue R-250 and bovine serum albumin (67,000), oxalbumin (43,000), carbonic anhydrase (30,000), and RNase A (13,700) (Pharmacia Fine Chemicals, Piscataway, N.J.) are used as molecular weight standards.

The SDS is then removed by passage through a DE-52 exchange column in the presence of 6 M urea. Fractions are collected from the column and are again examined by SDS-PAGE for either the 28 kDa or 60 kDa proteins as described in detail above. The proteins are further purified by gel filtration using a Bio Gel P1.5 column or by reverse phase HPLC.

EXAMPLE IV

A resulting solution of Example III containing the 28 kDa protein is injected into BALB/c mice at weekly intervals for four weeks. Spleen cells are used to prepare a single cell suspension which are fused with myeloma cells (P3X63-Ag 8.653). The myeloma cells are pelleted by centrifugation and are mixed with the washed spleen cells at a ratio of 7 spleen cells per myeloma cell and are pelleted by centrifugation and polyethylene glycol (35% w/vol in growth medium) is added to cause cell fusion. The resulting 40–80 hybrids are cultured for 6–10 days.

Hybridomas secreting antibodies reactive to the 28 kDa protein are selected by employing an enzyme-Linked immunosorbant assay in which antigen extracted by vortexing a cell suspension of *Legionella pneumophila* is used to coat the wells. Supernatants from the various hybridoma cell cultures are transferred to wells of the microtiter plate and allowed to react at 37° C. for 1 hour. THe wells are then washed with 0.05% Tween 20 in PBS (3X). Goat anti-mouse immunoglobulin conjugated with horseradish peroxidase is added to the wells and allowed to react for 30 minutes to 1 hour and following several washes, the chromagenic substrate (Bio-Rad Laboratories, Richmond, Calif.) and hydrogen peroxide are added and allowed to react for 20 minutes. The reaction is read by an ELISA reader or visually. Wells exhibiting a color change indicate that antibody produced by a particular hybridoma clone reacts with the antigen extracted from *Legionella pneumophila*.

These selected hybridomas are assayed for antibody production to a genus-specific epitope by employing procedures as described above with antigen extractions of both *L. micdadei* and *L. pneumiphila* (serogroup 2, Togus) prepared by vortexing the cells in bicarbonate buffer with glass beads present. Three hybrids show colorimetric reaction to both *L. micdadei* and serogroup 2 *L. pneumophila*. Culture of these hybridomas is continued and cell lines are on deposit at the Centers for Disease Control (Atlanta, Ga.) as cell lines 2x 2B2F4, 2S2D2D78 and 2S2D2C4B1. Antibodies from these cell lines react with all species of Legionella.

EXAMPLE V

The procedures of Example IV are employed with a resulting solution of Example III containing the 60 kDa protein. One hybrid cell line is identified as secreting an antibody to a genus specific epitope contained on the 60 kDa protein and is on deposit at the Center for Disease Control (Atlanta, Ga.) as cell line 2x 4-B8B2-H6, and at the American Type Culture Collection, 12301 Parklawn Drive, Rockville, Md. 20852, under accession No. ATCC HB9564. Antibodies secreted by this cell line react with all species of Legionella.

EXAMPLE VI

Polyclonal antibodies are raised in rabbits to the 28 and 60 kDa proteins by subcutaneous injection and subsequent booster injections until high titers are obtained. These antibodies are used in a capture ELISA assay for soluble antigen from blood, urine or serum samples. The polyclonal antibody is used to coat wells of microtiter plates. The antigen containing specimen (blood, urine or serum) is then added to the wells or tube and allowed to react for 1 hour. The wells or tubes are then washed to remove unbound material (3X) and then horseradish peroxidase conjugated monoclonal antibody harvested from cell line 2X 4-B8B2-H6 is then added to the wells and allowed to incubate for 30 minutes to 1 hour. The unbound monoclonal antibody is removed by 3 successive washes and the chromagenic substrate added for 20 minutes. If the wells of microtiter dishes exhibit color, this is a positive test for the presence of Legionella antigen.

EXAMPLE VII

Five liters of water from a cooling tower is filtered through a 0.45 uM filter. The filter is then placed in a sterile test tube to which has been added 2 ml of bicarbonate buffer and the material is vortexed to remove bacteria from the filter. The aqueous phase is transferred to a tube containing glass beads and the vortex step is repeated. Following low spin centrifugation to remove cells, the supernatant fluid is removed and tested for antigen by the procedures outlined in Example VI by antigen capture ELISA with horseradish peroxidase conjugated antibodies produced by cell line 2 X 2B2F4. A colorimetric reaction indicates the presence of Legionellae in the system.

While the forgoing examples disclosed monoclonal antibodies prepared by eliciting immunological responses to purified outer membrane proteins of *L. pneumophila*, it will be understood that outer membrane proteins from other species containing the same or similar epitopes can be employed to produce antibodies according to the invention. For example, the following outer membrane proteins of the other species can be employed similarly: *L. oakridgensis* (26 kDa), *L. micdadei* (26 kDa), *L. longbeachae* (28 kDa), *L. feeleyii* (28 kDa), *L. wadsworthii* (28 kDa), *L. dumoffi* (29 kDa), *L. bozemanii* (26–30 kDa), *L. gormanii* (28 kDa), *L. jordanis* (28 kDa).

The monoclonal antibodies of the present invention are well-suited for a wide variety of diagnostic and environmental tests for bacteria of the genus Legionella. Unlike known assays employing polyclonal antisera, the genus specific monoclonal antibodies of the present invention minimize problems with cross-reactivity with other bacteria. In addition, the monoclonal antibodies of the present invention can detect all species of Legionella and thus are useful for detecting all strains of Legionella and not only *L. pneumophila*. Although the genus-specific epitope is not exposed at the cell surface of all species, treatment such as mechanical disruption of the cells frees the antigen for detection. The antibodies are thus particularly well-suited for antigen capture assays with colorimetric reagents such as enzyme-linked immunoabsorbent assays. Assays employing the antibodies identify Legionellae with few false positives as is common with polyclonal sera.

Although particular embodiments of the invention have been described in the foregoing detailed description, it will be understood that the invention is capable of numerous modifications and substitutions without departing from the scope of the invention as set forth in the appended claims.

What is claimed:

1. A monoclonal antibody that specifically binds a genus-specific epitope present on outer membrane proteins of bacteria of the genus Legionella.

2. The monoclonal antibody of claim 1 wherein said outer membrane proteins are selected from the group consisting of a 60 kDa apparent molecular weight outer membrane protein of *Legionella pneumophila* and outer membrane proteins of other species of Legionella having genus-specific epitopes corresponding to that of the 60 kDa apparent molecular weight outer membrane protein of *Legionella pneumophila*.

3. An immortal, mammalian antibody-producing cell line that produces the monoclonal antibody of claims 1 or 2.

4. The monoclonal antibody of claim 1 that specifically binds the same epitope as the antibody produced by the cell line ATCC HB 9564.

5. An immortal, mammalian antibody-producing cell line that produces the monoclonal antibody of claim 4.

6. The cell line ATCC HB9564.

7. The monoclonal antibody produced by the cell line of claim 6.

* * * * *